United States Patent [19]

Bonato et al.

[11] Patent Number: 5,026,855

[45] Date of Patent: Jun. 25, 1991

[54] STEREOSPECIFIC PROCESS FOR THE PREPARATION OF FURO(3,4-C) PYRIDINE, ENANTIOMER, COMPOUNDS THUS OBTAINED AND THERAPEUTICAL COMPOSITIONS THEREOF

[75] Inventors: Marc Bonato, Aramon, France; Charles Eck, Schrewsbury, Mass.

[73] Assignee: Societe de Consels de Recherches et d Applications Scientifiques, France

[21] Appl. No.: 449,946

[22] Filed: Nov. 28, 1989

[30] Foreign Application Priority Data

Apr. 6, 1988 [GB] United Kingdom ................ 8808001

[51] Int. Cl.$^5$ ............................................ C07D 491/48
[52] U.S. Cl. .................................................... 546/116
[58] Field of Search ........................................ 546/116

[56] References Cited

U.S. PATENT DOCUMENTS

| | | | |
|---|---|---|---|
| 4,383,998 | 5/1983 | Esanu | 514/302 |
| 4,569,938 | 2/1986 | Esanu | 546/116 |
| 4,569,939 | 2/1986 | Esanu | 546/116 |
| 4,581,362 | 4/1986 | Esanu | 546/116 |
| 4,581,363 | 4/1986 | Esanu | 546/116 |
| 4,585,776 | 4/1986 | Esanu | 546/116 |
| 4,602,020 | 7/1986 | Esanu | 546/116 |
| 4,735,950 | 4/1988 | Esanu | 546/116 |

FOREIGN PATENT DOCUMENTS 204269 12/1986 European Pat. Off. .
09772 10/1989 PCT Int'l Appl. .
2137618 10/1984 United Kingdom .

OTHER PUBLICATIONS

Corey et al., Tetrahedron Letters, No. 11, pp. 809–812, 1976.
Terashima et al. J.C.S. Chem. Comm. 1980, pp. 1026–1027.

*Primary Examiner*—Cecilia Shen
*Attorney, Agent, or Firm*—Lucas & Just

[57] ABSTRACT

The present invention relates to stereospecific processes for the preparation of enantiomers of 3-substituted-furo[3,4-c]pyridine of formula I, wherein $R_3$, $R_4$ and $R_6$ stand for various substituents, comprising the steps of: oxidation of a racemic pyridine derivative of formula II, reduction of the resulting ketone with a reducing agent, sterospecific locking or blocking of the OH group of the enantiomer alcohol, opening of the acetonide ring and cyclization of the resulting compound.

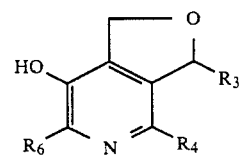

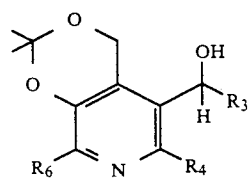

The present invention also relates to compounds thus obtained and therapeutical compositions thereof.

12 Claims, No Drawings

STEREOSPECIFIC PROCESS FOR THE PREPARATION OF FURO(3,4-C) PYRIDINE, ENANTIOMER, COMPOUNDS THUS OBTAINED AND THERAPEUTICAL COMPOSITIONS THEREOF

The present invention relates to stereospecific processes for the preparation of enantiomers of 3-substituted-furo[3-,4-c]pyridine of the general formula I

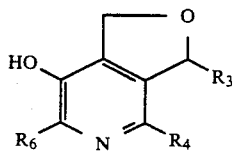

wherein $R_3$ stands for a straight chain saturated or unsaturated hydrocarbon group having from 1 to 5 carbon atoms, a heterocyclic group having up to 6 ring atoms, a phenyl or cyclohexyl group, a phenylalkyl group or a phenylalkenyl group, each of said groups being optionally substituted by one or more chlorine bromine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or an α- or β-alkoxy-N-pyrrolidinyl group in which the alkoxy group has from 1 to 5 carbon atoms; $R_4$ stands for a hydrogen or a halogen atom and $R_6$ stands for a straight chain or branched chain alkyl or alkenyl group having up to 6 carbon atoms, optionally substituted by a hydroxy, cyano, amino or substituted amino group or by an alkyl or alkenyl group having up to 4 carbon atoms.

The present invention also relates to the compounds thus obtained, either under the form of pure enantiomers or of mixtures thereof wherein one of the enantiomers is predominant.

In our previous U.S. Pat. Nos. 4,383,998, 4,581,363, 4,585,776, 4,569,938, 4,569,939, 4,581,362 and 4,659,719, all of which are incorporated herein by reference, were described families of such derivatives together with processes for obtaining the same. These derivatives included compounds where $R_3$ is a furyl or thienyl group. However, these processes led generally to racemic mixtures of the said compounds.

It has been found that in most cases, one of the optical isomers of a specific compound has a more important therapeutical activity than the other isomer. For that reason, it is of interest to find processes for a selective or at least predominant obtention of a specific isomer of each of these compounds.

The invention provides a stereospecific process for the preparation of a furo[3-,4]c-pyridine derivative of formula I as above defined, the process including the steps of (a) oxidizing a racemic pyridine derivative of the general formula II

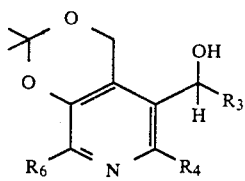

wherein $R_3$, $R_4$ and $R_6$ are as above defined by any usual oxidizing agent, such as, for instance, bipyridinium chlorochromate or sodium hypochlorite in an organic solvent.

(b) reducing the resulting ketone of the general formula III

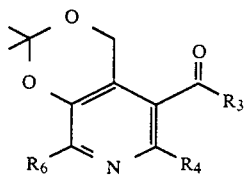

wherein $R_3$, $R_4$ and $R_6$ are as above defined with any chiral reducing agent such as B-Ipc-9-BBN (Alpine - borane, Aldrich), N,B Enantrane (Aldrich), Ipc$_2$BCl (Aldrich), BH$_3$-AMDPB (2:1) (see S.Itsuno, J.Chem.Soc., Chem.Comm. 1981, 315), (R,R)-2,5-dimethylborolane (see S.Masamune, J.Am Chem.Soc. 1986, 108, 7402), N,B Enantride (Aldrich), LiBH$_4$-DBC-t-BuOH (see K.Soal, J.Chem. Soc., Chem.Comm. 1984, 413), NaBH$_4$-IBA-DIPGF (see S.Itsuno, J.Chem.Soc., Perkin Trans.1, 1981, 900), K-Glucoride (see H.C.Brown, J.Org.Chem. 1986, 51, 1934), LiAlH$_4$-Darvon Alc (see H.Mosher, J.Am.Chem.Soc., 1972, 94, 9254), LiAlH$_4$-MEP-ArOH (see J.P.Vigneron, Tetrahedron 1976, 32, 939), LiAlH$_4$-Diamine (see M.Asami, Heterocycles, 1979, 12, 499), LiAlH$_4$-Aminobutanol (see T.Sato, Tet.-Letters 1982, 23, 4111), Binal H (see R.Noyori, J.Am.Chem.Soc. 1979, 101, 3129), LiAlH -DBP-EtOH (see K.Yamamoto, J.Chem.Soc., Chem. Comm. 1984,1490), LiAlH$_4$-MEP-NEA (see K.J.Koga, J.Chem Soc., Chem.Comm. 1980, 1026), LiAlH$_4$-MEP-EAP (see anaérobium brockii alcohol dehydrogenase, Signa Chem.Co.), CBS reagent (see E.J.Corey et al. J.Am. Chem.Soc., 1987, 109, 5551), MDBH$_2$ and MDBCl$_2$ (M.Bonato et al. in Press), or any appropriate catalyst for asymmetrical hydrogenation. All of the foregoing references are incorporated herein by reference.

The starting material II is an intermediate in the usual process for the preparation of the furo[3,4-c]pyridine derivatives of formula I.

The reduction of the ketone III with the selected reducing agent is suitably performed in tetrahydrofuran or any suitable mixture of ethers and hydrocarbons, and proceeds according to the following reaction scheme I, for giving the corresponding enantiomer alcohols in which $R_3$, $R_4$ and $R_6$ are as above defined.

SCHEME 1

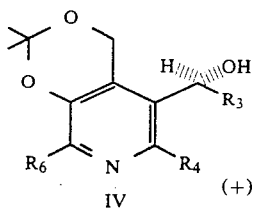

III + Selected stereospecific reducing agent

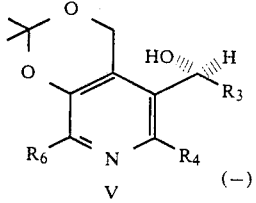

(c) stereospecific locking or blocking of the OH group of the selected enantiomer alcohol the locking agent may be an halogen, for instance, a chlorine atom substituted to the OH group; the blocking agent may be usual RX wherein X is a halogen and R is an aryl or an aralkyl or an alkyl or an alkoxy alkyl group (notably a methoxyethoxy-2 methyl group), all alkyl groups being up to $C_5$ or tertiary butyl silyl groups or being RCOX or $(RCO)_2X$ where X is a halogen and R stands for a lower alkyl group up to $C_5$.

(d) opening of the acetonide ring by protic acids with concommitant liberation of the $CH_2OH$ and OH groups on the pyridine ring ; in some cases, a protection of said $CH_2OH$ and OH groups may be necessary either by acetylation or by tosylation or by any equivalent method;

(e) cyclizing the resulting compound and, if necessary, deprotection of the phenoxy group.

In a first route (scheme II), the reduction of the ketone III by the selected reducing agent leads to the compounds IV or V, treatment of which with a chlorinating agent in an appropriate solvent gives compounds of the general formula VI or VII in which $R_3$, $R_4$ and $R_6$ are as above defined

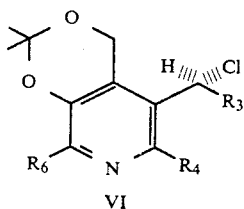 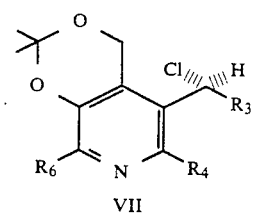

VI          VII

The chlorinating agent may be for instance triphenylphosphine with carbon tetrachloride as solvent or $SO_2Cl_2$ with methylene chloride as solvent; in the latter case, an addition of pyridine leads to an inversion of the stereochemical configuration of the chloro derivative at the beginning of the sequence of reactions. Bromine derivatives may be used instead of chlorine derivatives, with similar results.

The conversion of the compounds VI and VII to the corresponding furo[3,4-c]pyridine derivatives is achieved by cleavage of the acetonide cycle in acidic medium, followed by cyclization in protic solvents or mixtures thereof at room temperature or at gentle warming.

The sequence of reactions is illustrated as follows.

SCHEME 2
(−)-furo[3,4-c]pyridine derivatives

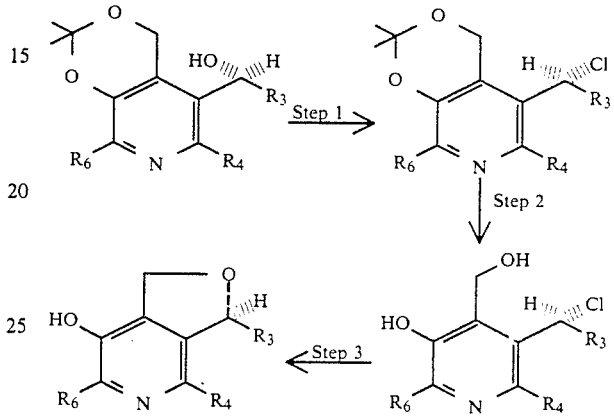

Care should be taken, during all the steps of the synthesis, to avoid the use of any method that would be likely to racemize the carbinol centre.

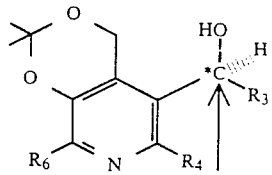

In a second route wherein the configuration of the asymmetrical carbon of the reagents is not affected, a first step consists in preliminary protecting of the secondary alcohol function by a stable group in acid medium. Protection groups may be ethers such as t-butyl diphenyl silyl or methoxyethoxy-2 methyl (MEM) can be used, as described by E.J. COREY, J.L. GRAS and P. ULRICH, Tetrahedron Letters, 1976, (11), 809 and S. HANESSIAN and P. LAVALLEE, Can. J. Chem., 1975, 53, 2975, both incorporated herein by reference, or esters such as acetate, benzoate and the like. The opening of the isopropylidene cycle is carried out by protic acids trifluoroacetic acid was choosen for this synthesis.

Alcohol protections in positions 3 and 4' of the pyridine ring are respectively obtained by acetylation and tosylation in the case of ether protection (scheme 3) or by tosylation alone (4'position) in the case of ester protection (scheme 4), according to conventional methods generally used in organic chemistry. Further deprotection when ethers are used can be made by various Lewis acids like $TiCl_4$ or $ZnBr_2$ in methylene chloride, as described by E.J. COREY, J.L. GRAS and P. ULRICH, Tetrahedron Letters, 1976, (11), 809 or trimethyl silyl chloride, sodium iodide, as described by J.H. RIGBY and J.Z. WILSON, Tetrahedron Letters, 1984, (14), 1429, incorporated herein by reference. Further deprotection when esters are used involves basic reagents such as MeOH/NH$_3$, MeOH/NaOMe, NaOH, K$_2$CO$_3$ for instance.

Finally, the cyclization and deprotection of the acetyl group leading to the final product is achieved by an attack from the corresponding alcoholate on the 4'carbon bearing the leaving group (tosyloxy).

The compounds IV and V may be converted to the corresponding predominantly (+) and predominantly (−) furo [3,4-c]pyridine derivatives.

SCHEME 4
(+)-furo[3,4-c]pyridine derivatives
Ester protection

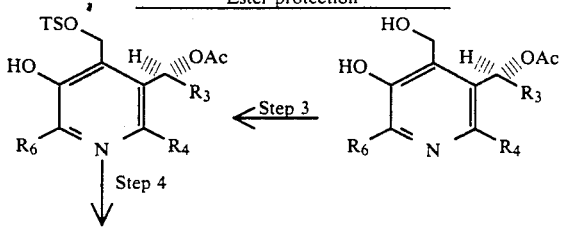

SCHEME 3
(−)-furo[3,4-c]pyridine derivatives
Ether protection

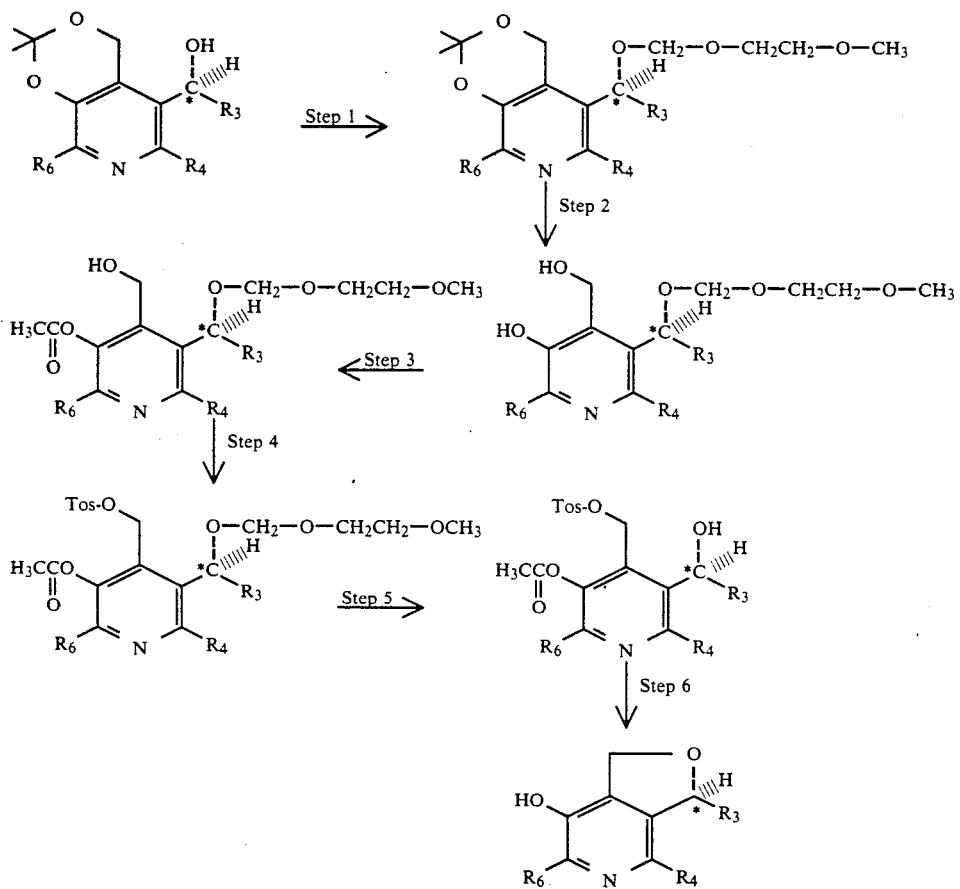

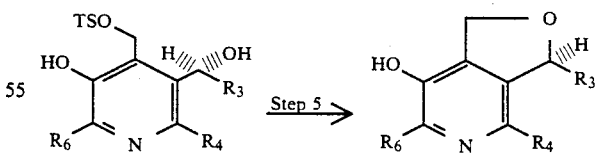

The method readily applies to various R$_3$ substituents and the invention will be better understood from the description of the synthesis of the (+) form of the furopyridine derivative wherein R$_4$ stands for H, R$_6$ stands for CH$_3$ and R$_3$ stands for p-chlorophenyl. The description is given by both routes.

The starting secondary alcohol may be obtained as described in the previous U.S. patent No. 4,383,998. When a (−) form of furo[3,4-c]pyridine derivative is to be prepared, the starting secondary alcohol of the fol-

SCHEME 4
(+)-furo[3,4-c]pyridine derivatives
Ester protection

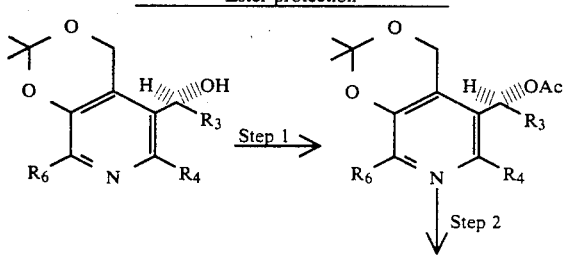

lowing step should be the corresponding (−) form instead of the (+) form.

PREPARATION OF
(+) or (−)-3-(4-chlorophenyl)-1,3-dihydro-7-hydroxy-6-methylfuro-[3,4-c]pyridine

EXAMPLE BY ROUTE 1

Step 1

2,2,8-trimethyl-5-(4-chloro-α-chlorobenzyl)-pyrido-[4,3-e]-1,3-dioxane 88 mg (0.275 mmole) of (+)-2,2,8-trimethyl-5-(4-chloro-α-hydroxybenzyl)-pyrido-[4,3-e]-1,3-dioxane are poured into a 5 ml flask, dissolved in 1 ml of methylene chloride and the flask is sealed under an atmosphere of nitrogen. 22 µl (0.27 mmole) of anhydrous pyridine are injected via a glass syringe. 36 µl (0.54 mmole) of thionyl chloride are then added dropwise. At disappearance (2 hours later) of the starting material (checked by TLC), the solvent is evaporated off under reduced pressure.

The residue is then dissolved in methylene chloride (50 ml), the pyridinium hydrochloride is filtered off and the solution is transferred to a separatory funnel. The methylene chloride fraction is washed with 2×10 ml of 2N HCl, the organic layer is dried over $Na_2SO_4$, filtered and evaporated to dryness on the roto vac (90 mg). Yield: 96.5%.

Step 2

(+)-3-(4-chlorophenyl)-1,3-dihydro-7-hydroxy-6-methylfuro3,4-c]pyridine 90 mg of (−)-2,2,8-trimethyl-5-(4-chloro-α-chlorobenzyl)-pyrido-[4,3-e]-1,3-dioxane are dissolved in 1 ml of TFA/$H_2O$ (9:1) and the rate of acetal cleavage is followed by HPLC. After 18 hours, the solvent is removed under a stream of nitrogen and reduced under pressure. The residue is dissolved in methanolic ammonia and brought to dryness under a nitrogen stream.

The crude residue is then dissolved in methanol (1 ml) and heated for 30 minutes. After cooling and filtration, a solid crystallizes out and its elemental analysis shows to be in perfect correspondence with the formula of the title compound. Yield: 66%, m=52 mg.

Starting with (−)-2,2,8-trimethyl-5-(4-chloro-α-hydroxybenzyl)-pyrido-[4,3-e]-1,3-dioxane, the corresponding (−) derivative is obtained with a similar yield.

EXAMPLE BY ROUTE 2 (Scheme 3)

Step 1

(+)-2,2,8-trimethyl-5-[4-chloro-α-(methoxyethoxy-2methoxy)-benzyl]-pyrido[4,3-e]-1,3-dioxane In a 0.1 litre reactor, the solution of 3.8 g (11.8 mmoles) of (+)-2,2,8-trimethyl-5-(4-chloro α-hydroxybenzyl)-pyrido-[4,3-e]-1,3-dioxane (90% (+), 10% (−)) is prepared in 24 ml of anhydrous tetrahydrofuran.

0.44 g of sodium hydride at 80% oil dispersion (14.8 mmoles) are added at 0° C. The reaction mixture is stirred at 20° C. for 4 hours, then cooled at 0° C. 2.2 g (17.8 mmoles) of methoxyethoxy-2 methyl chloride are added for 10 minutes. Stirring is maintained for 17 hours at 0° C.

A saturated solution of sodium bicarbonate is added and the organic phase obtained after decantation is dried over sodium sulphate.

After filtration and elimination of the solvent, an orange oil is purified by preparative HPLC. 2.4 g of a limpid yellow oil are obtained with a yield of 49.5%.

The identity and the structure of this compound were confirmed by proton $^1$H-NMR and microanalysis.

The enantiomeric composition achieved by chiral phase HPLC is of 90% (+), 10% (−).

Step 2

(+)-2-methyl-3-hydroxy-4-hydroxymethyl-5-[4-chloro-α- methoxyethoxy-2 methoxy)-benzyl-pyridine 2.4 g (5.8 mmoles) of (+)-2,2,8-trimethyl-5-[4-chloro α-(methoxyethoxy-2 methoxy)-benzyl -pyrido-[4,3-e]-1,3-dioxane are poured into a 50 ml reactor and treated with 20 ml of trifluoroacetic acid/water 1:1 at room temperature.

The reaction mixture is heated at 40° C. for 4 hours. The solvent is evaporated under vacuum. The resulting oil is dissolved in 25 ml of methanolic ammonia. The solvent is evaporated off under vacuum again and the residue is treated with 100 ml of dichloromethane. An insoluble is eliminated by filtration. The filtrate is concentrated under vacuum and 1.75 g of a brown oil is obtained. Yield: 81%.

The product is purified by HPLC; 1.12 g (overall yield 52%), is obtained as a white powder.

The identity and the structure of this compound were confirmed by proton $^1$H-NMR and microanalysis.

The enantiomeric composition cannot be achieved by chiral phase HPLC.

Step 3

(+)-2 methyl-3-acetyloxy-4-hyiroxymethyl-5-[(4-chloro-α-methoxyethoxy-2 methoxy)-benzyl]pyridine In a 50 ml reactor, 0.7 g (1.9 mmoles) of (+)-2-methyl-3-hydroxy-4-hydroxymethyl-5-[4-chloro-α-methoxyethoxy-2 methoxy)-benzyl]pyridine are dissolved in 15 ml of anhydrous toluene. 0.3 ml (2.46 mmoles) of N,N-dimethylaniline are added under stirring, followed by 0.5 ml (2.46 mmoles) of acetic anhydride.

The reaction mixture is kept at 40° C. for 6 hours, then cooled and washed with 3×50 ml of a sodium chloride saturated aqueous solution. The organic phase is dried over sodium sulphate, filtered and the solvent is eliminated under vacuum.

0.8 g of a brown oil are obtained and purified by HPLC. 0.39 g are recovered, yield 50%, as a yellow oil.

The identity and the structure of this compound were confirmed by $^1$H-NMR and by microanalysis.

The enantiomeric composition cannot be achieved by chiral phase HPLC.

Step 4

(+)-2-methyl-3-acetyloxy-4-tosyloxymethyl-5-[(4--chloro-α-methoxyethoxy-2-methoxy)-benzyl]pyridine In a 50 ml reactor are poured 0.3 g (1.5 mmole) of tosyl chloride in 10 ml acetone. A 0.3 g (0.7 mmoles) solution of (+)-2-methyl-3-acetyloxy-4-hydroxymethyl-5-[(4-chloro-α-methoxyethoxy-2-methoxy)-benzyl]-pyridine is added at room temperature in 10 ml acetone.

0.14 g (1 mmole) of potassium carbonate are then added. The reaction mixture is refluxed for 4 hours and filtered.

The filtrate is concentrated under vacuum. 0.76 g of a brown oil are purified by HPLC. 0.3 g of a thick yellow oil are obtained with a yield of 75%.

The identity and the structure of this compound were confirmed by proton $^1$H-NMR and by microanalysis.

The enantiomeric composition achieved by chiral phase HPLC is of 90% (+), 10% (−).

Step 5

(+)-2-methyl-3-acetyloxy-4-tosyloxymethyl-5-[4-chloro-α-hydroxybenzyl]pyridine

In a 0.1 litre reactor, under nitrogen circulation, the 0.3 g solution (0.53 mmoles) of (+)-2-methyl-3-acetyloxy-4-tosyloxymethyl-5-[(4-chloro-α-methoxyethoxy-2 methoxy)-benzyl]pyridine in 20 ml of CH$_3$CN is prepared at room temperature.

0.8 g (5.3 mmoles) of sodium iodide and 0.7 ml (5.3 mmoles) of chlorotrimethylsilane are added. The resulting orange suspension is stirred at room temperature for 1 hour. Hydrolysis of the reaction mixture is carried out with 20 ml of methanol at room temperature. The solvents are evaporated off and the remaining oil is taken with 50 ml of ethyl ether, washed twice with 50 ml of a sodium thiosulphate solution and twice with a sodium chloride saturated aqueous solution. The organic phase is dried over sodium sulphate.

After filtration and elimination of the solvent, a thick brown oil is recovered and purified by HPLC. 0.157 g are obtained as a white powder, with a yield of 63%.

The identity and the structure of this compound were confirmed by proton $^1$H-NMR and microanalysis.

The enantiomeric composition found by chiral phase HPLC is of 90% (+), 10% (−).

Step 6

(+)-3-(4-chlorophenyl)-1,3-dihydro-7-hydroxy-6-methylfuro-[3,4-c]pyridine

In a 10 ml flask, under nitrogen pressure, a solution of 100 mg (0.2 mmole) of (+)-2-methyl-3-acetyloxy 4-tosyloxymethyl-5-[4-chloro-α-hydroxybenzyl]pyridine in 1 ml of DMF is prepared.

12 mg (0.4 mmole) of sodium hydride (80% oil dispersion) are added under stirring at 20° C. The reaction mixture is stirred at room temperature for 1 hour, then diluted with 5 ml of water and acidified by 1 ml 6 N HCl.

The product is recovered by filtration and purified by HPLC. 44 mg are obtained as a white powder with a yield of 50%.

The identity and the structure of this compound were confirmed by proton $^1$H-NMR and microanalysis.

The enantiomeric composition achieved by chiral phase HPLC is of 80% (+), 20% (−).

This value represents an overall racemization based on starting (+)-2,2,8-trimethyl-5-(4-chloro α-hydroxy benzyl)-pyrido-[4,3-e]-1,3-dioxane of approximately 10%.

When starting with the corresponding (−) derivative, in step 1, the corresponding final (−) derivative is obtained with a slightly lower yield.

EXAMPLE BY ROUTE 2 (Scheme 4)

Step 1

2,2,8-trimethyl-5-(4-chloro-α-acetoxybenzyl)-pyrido-[4,3-e]-1,3-dioxane 210 mg (0.66 mmoles) of (+)-2,2,8-trimethyl-5-(4-chloro-α-hydroxybenzyl)-pyrido-[4,3-e]-1,3-dioxane are poured into a 2 ml vial and dissolved in 500 μl of pyridine and 110 μl of acetic anhydride (1.16 mmole). The reaction mixture is stirred for 18 hours, then poured into 30 ml of saturated NaHCO$_3$. The mixture is allowed to stir at room temperature for 1 hour, then extracted with 3×30 ml of CH$_2$Cl$_2$. The combined CH$_2$Cl$_2$ layers are washed with 3×20 ml of 2N HCl. The organic phase is dried over Na$_2$SO$_4$, filtered and the filtrate is evaporated to dryness. 24 g are obtained as a white solid with a yield of 100%.

This compound was shown to be homogeneous by silica TLC and chemically pure (99.1%) by HPLC. Optical purity is of 6.2% (−), 93.8% (+) by chiral HPLC.

Step 2

(+)-2-methyl-3-hydroxy-4-hydroxymethyl-5-[4-chloro-α-acetoxybenzyl]pyridine 0.24 g (0.66 mmoles) of (+)-2,2,8-trimethyl-5-(4-chloro-α-acetoxybenzyl)-pyrido-[4,3-e]-1,3-dioxane are poured into a 10 ml round bottomed flask and dissolved in 3.3 ml of TFA/H$_2$O (10:1). The reaction is allowed to stir at room temperature for 1.5 hours, the solvent is then removed by rotary evaporation. 1 ml of methanolic ammonia is added to the crude product (the excess of TFA being neutralized), then evaporated to dryness under high vacuum. The crude product was shown to contain 90% of the desired diol-acetate by HPLC along with 4.4% of unreacted starting material.

Steps 3 and 4

(+)-2-methyl-3-hydroxy-4-tosyloxymethyl-5-[4-chloro-α-hydroxybenzyl]pyridine 0.24 g (0.66 mmole) of (+)-2-methyl-3-hydroxy-4-hydroxymethyl-5-[4-chloro-α-acetoxybenzyl]pyridine are poured into a 25 ml round bottomed flask and dissolved in 10 ml of methylene chloride. 190 mg (1 mmole) of p-toluene sulphonyl chloride and 75 mg (1 mmole) of pyridine are then added. The reaction mixture is stirred at room temperature for 18 hours the solvent is then removed under reduced pressure. 5 ml of methanolic ammonia are added and the mixture is stirred at room temperature for 2 hours. The solvent is removed under vacuum, dissolved again in 1 ml of methanol and purified by silica TLC. 170 mg of the title compound were obtained as an off-white solid.

Step 5

(+)-3-(4-chlorophenyl)-1,3-dihydro-7-hydroxy-6-methylfuro[3,4-c]pyridine 62 mg (0.144 mmoles) of (+)-2-methyl-3-hydroxy-4-tosyloxymethyl-5-[4-chloro-α-hydroxybenzyl]pyridine are poured into a 2 ml vial and dissolved in 500 μl of HMPT. 14 mg (0.3 mmoles) of NaH (50% oil dispersion) are then added and the mixture is stirred at room temperature for 1 hour. The reaction mixture is diluted with 2.5 ml of H$_2$O and acidified with 2 drops of 6N HCl. The solid precipitate of the title compound which forms by gravity filtration is isolated. The crude solid is dissolved in methanol, spotted on a 1000μ silica TLC plate, and eluted in CH$_2$Cl$_2$/MeOH (7:1). The major UV band which co-eluted with a spot of authentic (+)-3-(4-chlorophenyl)-1,3-dihydro-7-hydroxy-6-methylfuro-[3,4-c]pyridine is excised and the organic material is isolated by thorough washing of the silica with methanol. The methanol filtrate is evaporated, which gives 27 mg of a white solid. This compound was shown to be the title compound by co-elution with authentic (+)-3-(4-chlorophenyl)-1,3-dihydro-7-hydroxy-6-methylfuro-[3,4-c]pyridine on TLC and HPLC.

The optical purity of the sample, assayed by chiral phase HPLC, is of 14.6% (−), 85.4% (+).

This value represents an overall racemization of 7.5% based on starting (+)-2,2,8-trimethyl-5-(4-chloro-α-hydroxybenzyl)-pyrido-[4,3-e]-1,3-dioxane.

(+)-3-(4-chlorophenyl)-1,3-dihydro-7-hydroxy-6-methylfuro-[3,4-c]pyridine has been prepared from (+)-2,2,8-trimethyl-5-(4-chloro-α-hydroxybenzyl)-pyrido-[3,4-e]-1,3-dioxane in an approximate 45% overall yield for the 5 step sequence.

The preparation of (-)-3-(4-chlorophenyl)-1,3-dihydro-7-hydroxy-6-methylfuro-[3,4-c]pyridine from (−)-2,2,8-trimethyl-5-(4-chloro-α-hydroxybenzyl)-pyrido-[1,3-dioxane by the same route was obtained with a slightly better overall yield (48%).

The compounds obtained according to this invention are interesting in the various pharmaceutical fields described in the previous patents mentioned on page 2.

Accordingly, this invention also relates to therapeutic compositions, one active ingredient therein being an enantiomer or a mixture of enantiomers wherein one enantiomer is substantially predominant.

The appropriate administration modes are described in the patents previously mentioned on page 2, but dosage is lower than in said patents, which is due to the enhanced activity of the selected enantiomer or of the enantiomer mixtures in which the said enantiomer is predominant.

This is shown, for instance, by the comparative diuretic action on normal WKY rats of the two enantiomer forms, with the corresponding racemic. The experiment was conducted on batches of 10 rats with doses of 10 or 20 mg/kg, per os, each animal receiving 2.5 ml per 100 g of weight, of physiologic serum, either pure, for control batch, or supplemented with the appropriate quantity of the product to be tested, for animals treated by the racemic or by each one of the enantiomers.

The results were reported in the following table. It can be observed that the (+) isomer, at 10 mg/kg, is at least as active as the racemic at 20 mg/kg and that at such doses, it is 58% better for the Na+/K+elimination rate. Furthermore, the dose/effect ratio shows a maximum and the optimal dose for normal rats is of about 6 mg/kg per os.

A similar experiment was conducted on genetically hypertensive SHR-SP rats at the dose of 3 mg/kg, per os. For the enantiomers as well as for the racemic, the volumes of urine collected in 6 hours were 10% superior for the (+) derivative in comparison with the racemic.

| Products | | Controls | Racemic 20 mg/Kg PO | Isomer (+) 10 mg/Kg PO | Isomer (+) 20 mg/Kg PO | Isomer (−) 10 mg/Kg PO | Isomer (−) 20 mg/Kg PO |
|---|---|---|---|---|---|---|---|
| urine volume | ml/6 h | 1.71 ± 0.180 | 4.71 ± 0.314 *** | 4.76 ± 0.338 *** | 4.44 ± 0.467 *** | 2.48 ± 0.245 NS | 2.72 ± 0.174 * |
| | % Var. | — | 175 | 178 | 160 | 45 | 59 |
| uric acid | $10^{-3}$ mmol/ 6 h | 3.15 ± 0.269 | 2.35 ± 0.142 *** | 2.29 ± 0.103 *** | 1.94 ± 0.138 *** | 2.49 ± 0.101 ** | 2.5 ± 0.188 ** |
| | % Var. | — | −25 | −27 | −38 | −21 | −21 |
| Cl− | $10^{-3}$ mEq/ 6 h | 356.6 ± 31.56 | 896.5 ± 32.67 *** | 869.2 ± 33.91 *** | 879.9 ± 41.70 *** | 467.5 ± 26.26 * | 517 ± 20.96 *** |
| | % Var. | — | 151 | 144 | 147 | 31 | 45 |
| K+ | $10^{-3}$ mEq/ 6 h | 124.2 ± 12 | 195.6 ± 11.56 *** | 169.4 ± 15.65 ** | 180.6 ± 13.58 ** | 156.7 ± 11.6 NS | 159.4 ± 12.42 NS |
| | % Var. | — | 57 | 36 | 45 | 26 | 28 |
| Na+ | $10^{-3}$ mEq/ 6 h | 282.1 ± 24.57 | 780.5 ± 33.01 *** | 767.7 ± 31.22 *** | 749.1 ± 42.73 *** | 387 ± 27.37 * | 422.5 ± 20.56 ** |
| | % Var. | — | 177 | 172 | 166 | 37 | 50 |
| $\frac{Na+}{K+}$ | Ratio | 2.25 ± 0.222 | 4.08 ± 0.147 *** | 5.12 ± 0.525 *** | 4.34 ± 0.268 *** | 2.55 ± 0.163 NS | 2.83 ± 0.200 NS |
| | % Var. | — | 81 | 128 | 93 | 13 | 26 |

PRESENTATION

The preferred administration mode is tablets and capsules. For tablets, each dosage unit contains from 5 to 100 mg or, preferably, 10 to 25 mg of the active principle associated with an appropriate carrier as starch for instance.

POSOLOGY

In human therapy, the doses to be used are from 50 to 150 mg/day for at least one week, and preferably for longer periods of time.

We claim:

1. Stereospecific process for the preparation of enantiomers of 3-substituted-furo-[3,4-c]pyridine of the formula I

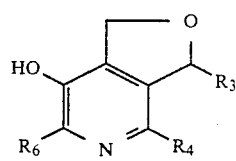

wherein
R3 stands for a straight chain saturated or unsaturated hydrocarbon group having from 1 to 5 carbon atoms, a furyl or thienyl group, a phenyl or cyclohexyl group, a phenylalkyl group or a phenylalkenyl group, each of said groups being optionally substituted by one or more chlorine, bromine or fluorine atoms, trifluoromethyl groups, alkyl groups having from 1 to 5 carbon atoms, alkoxy groups having from 1 to 5 carbon atoms, dialkylamino groups in which each alkyl group has from 1 to 5 carbon atoms or an α- or β-alkoxy-N-pyrrolidinyl group in which the alkoxy group has from 1 to 5 carbon atoms; $R_4$ stands for a hydrogen or a halogen atom; and $R_6$ stands for a straight chain or branched chain alkyl or alkenyl group having up to 6 carbon atoms, optionally substituted by a hydroxy, cyano, amino or amino group substituted by an alkyl or alkenyl group having up to 4 carbon atoms, comprising the steps of (a) oxidizing a racemic pyridine derivative of the formula II

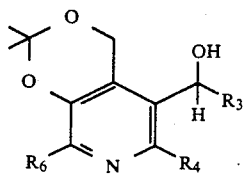

wherein $R_3$, $R_4$ and $R_6$ are as above defined;

(b) reducing the resulting ketone of the formula III

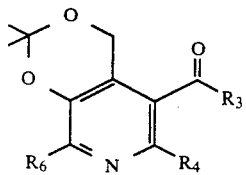

wherein $R_3$, $R_4$ and $R_6$ are as above defined with a chiral reducing agent or a catalyst for asymmetrical hydrogenation, which gives, according to the selected chiral reducing agent or catalyst, the following compounds:

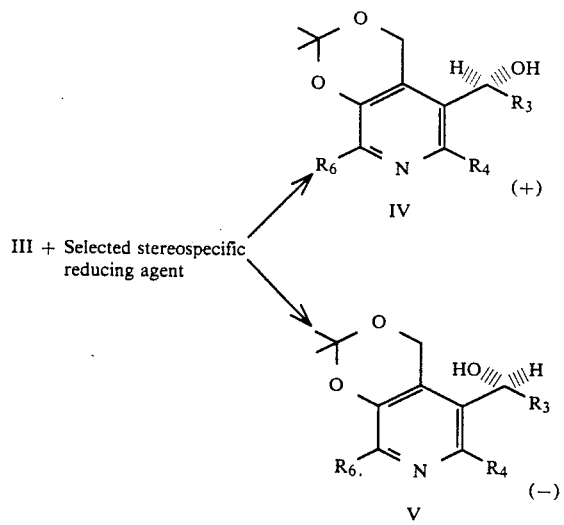

(c) stereospecific locking or blocking of the OH group of the selected enantiomer alcohol;

(d) opening of the acetonide ring by protic acids with concomitant liberation of the $CH_2OH$ and OH groups on the pyridine ring; and (e) cyclizing the resulting compound.

2. The process of claim 1 wherein the locking agent has a halogen atom substituted for the hydroxy group at the carbinol centre of the enantiomer alcohol.

3. The process of claim 2 wherein halogen is chlorine atom.

4. The process of claim 3 wherein the chlorinating agent is selected between triphenylphosphine and $SO_2Cl_2$.

5. The process of claim 1 wherein the blocking agent is RX, X being an halogen and R being an aryl or an aralkyl or an alkyl or an alkoxy alkoxy alkyl group, all alkyl groups being up to $C_5$, or tertiary butyl silyl group.

6. The process of claim 4 wherein the blocking agent is a methoxyethoxy-2 methyl group.

7. The process of claim 1 wherein the blocking agent is RCO X or $(RCO)_2$, where X is an halogen and R stands for a lower alkyl group up to $C_5$.

8. The process of claim 5 wherein the blocking agent is an acetoxy group.

9. (+) or mixtures of predominant (+) enantiomers of the 3-substituted-furo-[3,4-c]pyridine of the formula I

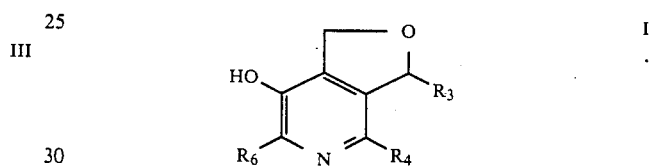

wherein $R_3$ stands for a straight chain saturated or unsaturated hydrocarbon group having from 1 to 5 carbon atoms, a furyl or thienyl group a phenyl or cyclohexyl group, a phenylalkyl group or a phenylalkenyl group, each of said groups being optionally substituted by one or more chlorine bromine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or an α- or β-alkoxy-N-pyrrolidinyl group in which the alkoxy group has from 1 to 5 carbon atoms; $R_4$ stands for a hydrogen or a halogen atom and $R_6$ stands for a straight chain or branched chain alkyl or alkenyl group having up to 6 carbon atoms, optionally substituted by a hydroxy, cyano, amino or amino group substituted by an alkyl or alkenyl group having up to 4 carbon atoms.

10. (+) or mixtures of predominant (+) enantiomers of the 3-substituted-furo-[3,4-c]pyridine of claim 9 wherein $R_3$ stands for p-chlorophenyl, $R_4$ stands for H and $R_6$ stands for $CH_3$.

11. Therapeutical compositions, the active ingredient therein being a sufficient amount of the compound according to claim 9, together with an appropriate diluent or carrier.

12. Therapeutical compositions according to claim 11, in which the active ingredient per dosage unit contains 5 to 100 mg of (+)-3-(4-chlorophenyl)-1,3-dihydro-7-hydroxy-6-methylfuro-[3,4-c]pyridine, or a mixture wherein this enantiomer is predominant.

* * * * *

UNITED STATES PATENT AND TRADEMARK OFFICE
CERTIFICATE OF CORRECTION

PATENT NO. : 5,026,855
DATED : June 25, 1991
INVENTOR(S) : Marc Bonato et al

It is certified that error appears in the above-identified patent and that said Letters Patent is hereby corrected as shown below:

On the title page, item [54], lines 1-5, and col. 1, lines 2-6, the title should read as follows:

--STEREOSPECIFIC PROCESS FOR THE PREPARATION OF FURO [3,4-c] PYRIDINE ENANTIOMERS, COMPOUNDS THUS OBTAINED AND THERAPEUTICAL COMPOSITIONS THEREOF--.

Column 1, line 63, change "furo[3-,4]c-pyridine" to --furo[3,4-c]pyridine--.

Column 2, line 27, after "such as" insert --:--.

Column 2, line 46, change "LiAlH" to --LiAlH$_4$--.

Column 2, line 50, after "(see" insert --S. Terashima, Chem. Letters 1984, 239), TBADH (thermo- --.

Column 2, line 51, change "Signa" to --Sigma--.

Column 3, line 29, after "alcohol" insert --;--.

Column 3, line 33, after "alkoxy" insert --alkoxy--.

Column 3, line 39, change "concommitant" to --concomitant--.

Column 4, line 54, change "choosen" to --chosen--.

Column 7, line 33, change "methylfuro3,4-c]pyridine" to --methylfuro-[3,4-c]pyridine--.

Column 7, line 54, change "2methoxy" to --2 methoxy--.

UNITED STATES PATENT AND TRADEMARK OFFICE
CERTIFICATE OF CORRECTION

PATENT NO. : 5,026,855
DATED : June 25, 1991                                        Page 2 of 3
INVENTOR(S) : Marc Bonato et al.

It is certified that error appears in the above-identified patent and that said Letters Patent is hereby corrected as shown below:

Column 8, line 12, change "benzyl-pyridine" to --benzyl]pyridine--.

Column 8, line 14, change "benzyl -pyrido" to --benzyl]-pyrido--.

Column 8, line 35, change "(+)-2" to --(+)-2- --.

Column 8, line 36, change "hyiroxymethyl" to --hydroxymethyl--.

Column 10, line 41, after "18 hours" insert --;--.

Column 10, line 51, change "methylfuro[3,4-c]" to --methylfuro-[3,4-c]--.

Column 11, line 41, change "[1,3-dioxane" to --[4,3-e]-1,3-dioxane--.

Column 14, line 17, change "(RCO)$_2$" to --(RCO)$_2$X--.

UNITED STATES PATENT AND TRADEMARK OFFICE
CERTIFICATE OF CORRECTION

PATENT NO. : 5,026,855

DATED : June 25, 1991

INVENTOR(S) : Marc Bonato et al

It is certified that error appears in the above-identified patent and that said Letters Patent is hereby corrected as shown below:

Column 14, line 35, after "group" insert --,--.

Signed and Sealed this

Seventeenth Day of November, 1992

Attest:

DOUGLAS B. COMER

*Attesting Officer*   Acting Commissioner of Patents and Trademarks